United States Patent [19]

Levine

[11] Patent Number: 5,328,442
[45] Date of Patent: Jul. 12, 1994

[54] SYSTEM AND METHOD FOR STIMULATING A HEART HAVING UNDERGONE CARDIAC MYOPLASTY USING A SINGLE-CHAMBER PACEMAKER

[75] Inventor: Paul A. Levine, Santa Clarita, Calif.

[73] Assignee: Siemens Pacesetter, Inc., Sylmar, Calif.

[21] Appl. No.: 979,502

[22] Filed: Nov. 20, 1992

[51] Int. Cl.$^5$ ............................................. A61N 1/36
[52] U.S. Cl. ..................................................... 600/17
[58] Field of Search ................. 128/419 PG, 419 R; 600/16, 17

[56] References Cited

U.S. PATENT DOCUMENTS

| | | | |
|---|---|---|---|
| 3,974,834 | 8/1976 | Kane | 128/418 |
| 4,214,594 | 7/1980 | Little | 128/786 |
| 4,402,329 | 9/1983 | Williams | 128/785 |
| 4,411,268 | 10/1983 | Cox | 128/421 |
| 4,466,441 | 8/1984 | Skubitz et al. | 128/419 |
| 4,643,201 | 2/1987 | Stokes | 128/786 |
| 4,712,555 | 12/1987 | Thornander et al. | 128/419 |
| 4,764,132 | 8/1988 | Stutz, Jr. | 439/810 |
| 4,774,952 | 10/1988 | Smits | 128/419 |
| 4,848,346 | 7/1989 | Crawford | 128/419 |
| 4,940,052 | 7/1990 | Mann et al. | 128/419 |
| 5,069,680 | 12/1991 | Grandjean | 600/16 |

OTHER PUBLICATIONS

Calfee, Richard V. et al., "A Voluntary Standard for 3.2 mm Unipolar and Bipolar Pacemaker Leads and Connectors," *PACE*, vol. 9, pp. 1181-1185 (Nov.-Dec. 1986, Part II).

Chiu, Ray Chu-Jeng M.D., Ph.D. et al., *Transformed Muscle for Cardiac Assist and Repair*, Chapters 21-23, pp. 231-251 (Futura Publishing Co.) (Mt. Kisco, N.Y.—1990).

*Primary Examiner*—William E. Kamm
*Attorney, Agent, or Firm*—Lisa P. Weinberg; Bryant R. Gold

[57] ABSTRACT

A bifurcated lead adapter or lead used with an implantable stimulation device, such as a pacemaker, forms part of a stimulation system and method that senses depolarization of the ventricular muscle tissue, and in response thereto, generates a stimulus (composed of a single pulse or multiple closely-spaced pulses) that is delivered to translocated muscle tissue wrapped around the ventricle of the heart, thereby causing the translocated muscle tissue to contract in synchrony with the sensed ventricular depolarization. In one embodiment, a pacemaker operates in the single-chamber triggered stimulation mode analogous to VVT mode. A bifurcated bipolar lead adapter has a proximal connector that is connected to the pacemaker's bipolar female input/output connector. The adapter couples the anode electrode of the pacemaker's bipolar input/output connector to a first female distal connector, and couples the cathode electrode of such bipolar input/output connector to a second female distal connector. Two conventional unipolar stimulation leads, with or without active fixation means, are connected to the female distal connectors of the adapter. The tip electrode of one lead is coupled to ventricular tissue in conventional manner. The tip electrode of the other lead is coupled to the translocated muscle tissue.

21 Claims, 4 Drawing Sheets

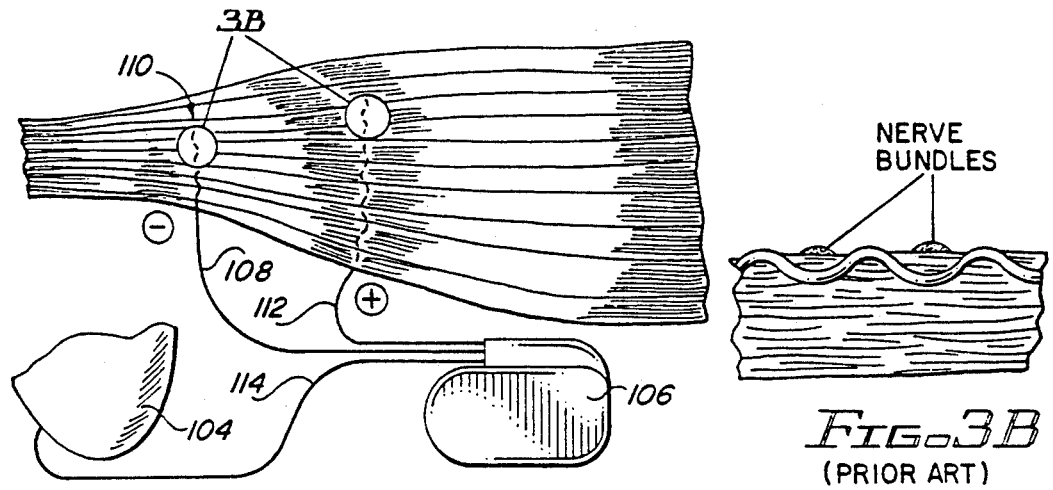
FIG.-3A
(PRIOR ART)
FIG.-3B
(PRIOR ART)
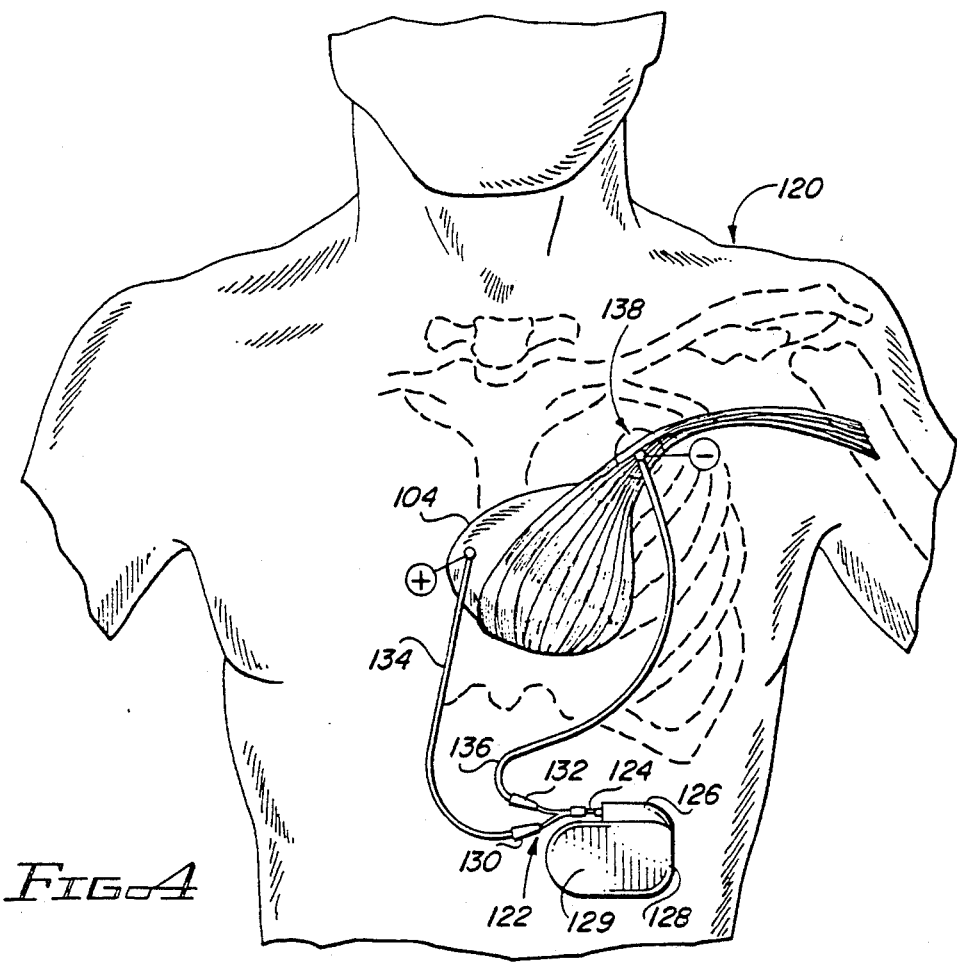
FIG.-4

SYSTEM AND METHOD FOR STIMULATING A HEART HAVING UNDERGONE CARDIAC MYOPLASTY USING A SINGLE-CHAMBER PACEMAKER

FIELD OF THE INVENTION

The present invention relates to a system and method of stimulating a heart, and more particularly to a system and method of coordinating the stimulation of the heart in conjunction with translocated muscle tissue wrapped around the heart. The present invention further relates to an implantable stimulation lead, or lead adapter for use with conventional stimulation leads, that allows a conventional pacemaker operating in a triggered mode to sense a tissue depolarization and thereafter deliver a stimulation pulse to the translocated muscle tissue wrapped around the heart.

BACKGROUND OF THE INVENTION

Congestive heart failure (CHF) is a group of symptoms (or symptom complex) due to the heart not being able to adequately pump blood to meet the demands of the body/tissues. A result of this inability to adequately pump blood is that the tissues behind the pump (i.e., the lungs with respect to the left ventricle) becomes congested or filled with excess fluid, hence the name congestive heart failure. As blood backs up behind the left ventricle, the lungs become engorged and stiff with the patient complaining of shortness of breath. If the right ventricle fails, the backed-up blood causes the organs in the abdomen to become engorged with blood, and also causes the legs to become swollen. As the heart's ability to pump blood progressively decreases, the patient becomes increasingly more tired and fatigued.

Congestive heart failure can be due to any number of causes, such as dilated cardiomyopathy, hypertrophic cardiomyopathy, valvular dysfunction or volume overload with a normal heart as in chronic renal failure. Among these known causes, only dilated cardiomyopathy is treated with cardiomyoplasty. For the purpose of this patent application, congestive heart failure as used herein will mean congestive heart failure due to dilated cardiomyopathy.

The causes of congestive heart failure are multiple. In the United States and Europe, the most common cause is coronary artery disease resulting in myocardial infarctions (heart attacks) which destroy a portion of the heart muscle, thereby weakening the heart. The heart may also be affected by a vital or other infections (such as Trypanosoma cruzi, most common in South America), toxins (the most common of which is alcohol), or unknown causes (referred to as "idiopathic"). It is estimated that there are over 100,000 new patients each year with congestive heart failure.

At the present time, the therapy for congestive heart failure is primarily pharmacological, with some major recent success utilizing the angiotensin converting enzyme (ACE) inhibitors. However, the use of ACE inhibitors does not correct the problem; it only treats it. Hence, the basic pathophysiologic process continues, and eventually pharmacological therapy will be ineffective.

A popular therapy for advanced congestive heart failure, particularly in younger individuals, is cardiac transplant. However, this therapy is very limited because it requires a major surgical procedure, is very expensive, and acceptable donor hearts are in very limited supply. Hence, what is needed is a more viable therapy for advanced congestive heart failure.

In recent years, it has been postulated that strong skeletal muscle tissue could be trained to repeatedly contract, and yet not fatigue. If such "trained" muscle tissue were translocated within a patient so that it were wrapped around the failing heart, then such translocated muscle tissue could assist, if not take over for, the failing cardiac muscle tissue, thereby allowing the heart to better perform its function of a pump. The idea is that when the stronger skeletal muscle tissue contracts, after it has been wrapped around the heart, it compresses the heart from the outside, thereby augmenting the vigor with which the heart ejects (pumps) blood. Such translocation of skeletal or other strong muscle tissue around the heart is referred to as "cardiac myopiasty".

Cardiac myopiasty offers the advantage of avoiding some of the more common and serious problems associated with cardiac transplant, namely a limited supply of donor hearts, rejection of the donated heart, or infection due to the immunosuppressive agents used to prevent rejection. Advantageously, there is almost always some healthy skeletal or other muscle tissue of the patient that may be translocated and wrapped around the patient's heart. Thus, unlike transplanted hearts (which are in limited supply; are usually only located after diligent searching and long waiting; and, when found, must still be safely transported to a medical facility where the transplant operation can take place), the skeletal or other muscle tissue is with the patient at all times. Further, because the translocated muscle tissue is the patient's own tissue, there is no risk of rejection, as commonly occurs when a heart is transplanted. Using translocated muscle tissue also eliminates the need for lifetime pharmacological therapy with agents designed to prevent rejection, yet which agents have a high incidence of side effects (such as atherosclerosis, altered post-immunocompetence resulting in infection and malignancy). Such agents also tend to be very expensive. Hence, cardiac myopiasty offers a very attractive alternative to cardiac transplant. In order for cardiac myopiasty to be a viable option for a patient suffering from congestive heart failure, there is a need in the art for a quick and safe method or technique of training the muscle tissue that has been translocated around the heart. Such training of the muscle tissue involves repetitive stimulation of the muscle tissue with a stimulation device, e.g., a pulse generator.

Heretofore, such stimulation of the muscle tissue has involved two different pacing modes. Initially, to "train" the muscle, a pulse generator has been used with the stimulating electrode in contact with either the muscle or the neurovascular bundle supplying the muscle. The muscle tissue is then stimulated by delivering output pulses at progressively more rapid rates over a period of weeks. After such initial training, the muscle tissue is translocated so as to be wrapped around the heart. The tissue is then stimulated with a dual-chamber pulse generator. One channel of the dual-chamber pulse generator is used for cardiac sensing and pacing and is electrically connected to either the ventricle or the atrium using either a conventional endocardial or myocardial lead. The other channel is electrically connected to the translocated muscle tissue using, either myocardial or intramuscular lead(s).

There are two types of pulse generators currently in use to provide the dual-chamber stimulation: a demand-type "DDD" pacemaker, and a dedicated cardiac myostimulator. A myostimulator sytem typically comprises a first intramuscular lead near the nerve branches of the translocated muscle tissue, a second intramuscular lead placed distal from the first to act as the anode, and a third lead for sensing native depolarizations of the heart.

Unfortunately, there are several disadvantages associated with using a myostimulator system to train the translocated muscle tissue. First, such system requires a special purpose pulse generator designed to deliver burst pacing. Second, such burst pacing rapidly depletes the battery longevity of the device, causing it to have a relatively short life. Third, the size, weight and cost of the myostimulator device is very high.

The other type of dual-chamber pulse generator currently used to stimulate the translocated muscle tissue is the demand-type DDD pacemaker. Such dual-chamber pacemaker is configured such that one channel (the atrial channel) senses the native depolarization of the atrium (or paces the atrium, as required), and the other channel paces the translocated muscle tissue one AV delay thereafter. Thus, the synchronization delay is the dual-chamber pacemaker's programmed AV interval, and is set equal to the patient's native PR interval. Thus, as the atrium contracts or is stimulated, the dual-chamber pacemaker issues a stimulation pulse one AV interval thereafter, thereby stimulating the translocated muscle tissue at approximately the same time that the ventricle contracts. In this way, the strong skeletal muscle tissue is stimulated to squeeze the ventricle, helping to eject or pump the blood, in synchrony with the heart's natural rhythm.

Disadvantageously, the use of a dual-chamber pulse generator to stimulate the translocated muscle tissue in the above-described manner suffers from many of the same drawbacks as using a myostimulator pulse generator, i.e., the size, weight and cost of a dual-chamber pulse generator is very high.

In addition, in a patient with congestive heart failure, the failing ventricle may cause a backup in pressure which, in turn, may cause a high pressure buildup in the atria, and may cause the atria to dilate. When this occurs, a very common response is atrial fibrillation, which is a very rapid and disorganized (ineffective) rhythm of the atria. Such rapid atrial rhythm is not a coordinated rhythm and is contraindicated for dual-chamber pacing. Hence, the dual-chamber DDD pacemaker (which is able to sense the atrial contractions) has no way to determine a reference point from which to measure the AV interval, and is accordingly not able to properly synchronize the stimulation of the translocated skeletal tissue with the ventricular contraction. In addition, patients with congestive heart failure have frequent ectopic ventricular beats which are not coordinated with native atrial activity.

What is needed, therefore, is a device that can effectively train translocated muscle tissue, does not require a dual-chamber pulse generator; has a long life; has a size, weight and cost that is significantly less than that of either dual-chamber pulse generators or myostimulator devices, and does not induce any other type of arrhythmias.

Thus, there is a need in the art for a technique of stimulating translocated muscle tissue placed around the heart in a coordinated manner in synchrony with the ventricle's natural rhythm.

SUMMARY OF THE INVENTION

The above-identified needs are met by the present invention which provides a stimulation system and method that advantageously directs a stimulation pulse to the translocated muscle tissue in response to sensed ventricular activity.

The present invention includes a pulse generator, means for sensing the native heartbeat, and means for simultaneously delivering an output pulse of the pacemaker to a desired stimulation location. More specifically, the present invention utilizes a single-chamber bipolar pacemaker operating in a triggered mode (e.g., the VVT mode). In the VVT mode, stimulation pulses are generated or "triggered" upon the electrical sensing of depolarization signals (R-waves) in the ventricle. In the prior art, the triggered stimulation was used exclusively for diagnostic purposes (e.g., to verify proper sensing by marking sensed cardiac signals with a pulse) and generally not used for long-term pacing since the triggered pulse accelerated battery depletion. The present invention advantageously redirects the triggered stimulation pulse to the translocated muscle tissue to contract in synchrony with the natural cardiac tissue around which the translocated tissue is wrapped. Advantageously, the pulse generator is an off-the-shelf single-chamber pacemaker, thereby allowing it to be smaller and less costly than either a dual-chamber device or a custom myopiasty stimulator. Furthermore, the single-chamber pacemaker may be easily modified to programmably generate either a single pulse or a train of closely-spaced pulses.

The delivery of the stimulation pulse in synchrony with sensing ventricular depolarization is achieved in one of two ways. In a preferred delivery scheme, a standard bifurcated bipolar lead adapter couples the bipolar output channel of a single-chamber pacemaker to two standard unipolar leads. The distal tip electrode of one unipolar lead is placed at the neurovascular site of the translocated muscle tissue. The distal tip electrode of the other unipolar lead is placed in contact with the right (or left) ventricle of the heart. For stimulation purposes, the tip electrode in contact with the translocated muscle tissue is configured to function as the cathode (−) and the return electrode, or anode (−), may be programmably selected to be either the pacemaker case (i.e., in a unipolar mode) or the tip electrode in contact with the ventricular tissue (i.e., in a bipolar mode). Sensing may be likewise programmed between the tip electrode in contact with the ventricular tissue and the pacemaker case (i.e., in a unipolar mode) or between the tip electrode in contact with the right ventricle and the tip electrode in contact with the translocated muscle tissue (i.e., in a bipolar mode).

In an alternate delivery scheme, the stimulation device still operates in a single-chamber triggered mode, however, a custom lead adapter is used which couples the output channel of single-chamber pacemaker to simultaneously stimulate two widely spaced sites. The distal tip of a first unipolar lead is placed at the neurovascular site of the translocated muscle tissue and is configured to function as a cathode (−). The distal tip of a second lead is placed in contact with the right ventricle of the heart and is also configured to function as a cathode (−). (Note that the second lead is preferably a bipolar lead so that bipolar sensing is possible, but may be a unipolar lead.) Thus, the single-chamber pacemaker is configured to sense in the right ventricle like a conventional pacemaker, trigger a stimulation pulse in the right ventricle, and simultaneously trigger a stimulation pulse to effect contraction of the translocated muscle tissue. Since the ventricular tissue is refractory at this time, the triggered stimulation pulse to the ventricle has no effect thereon.

A stimulation system made in accordance with the present invention is designed for a patient who has received cardiac myopiasty (translocated muscle tissue around the heart). Such system may be characterized as including: (1) a single-chamber implantable pulse generator having means for sensing ventricular depolarization at a ventricular tissue location and means for generating a stimulation pulse in response thereto; and (2) delivery means for delivering a stimulation pulse generated by the stimulation device to the translocated muscle tissue. With such system, the translocated muscle tissue placed around the patient's heart may be stimulated to contract at the same time that the ventricular cardiac tissue is sensed to depolarize.

As indicated, in the preferred embodiment, the delivery means comprises a standard bifurcated bipolar lead adapter and two standard unipolar stimulation leads. The bifurcated lead adapter made in accordance with the preferred embodiment is designed for use with a stimulation device, such as a pacemaker, wherein the stimulation device has a single bipolar in-line output connector (i.e., a connector having a cathode (−) and an anode (+) terminal within a single channel, or receptacle). The bifurcated bipolar lead adapter may be characterized as a Y-shaped insulated conductor having two distal female connectors and a single proximal male connector which is adapted to be inserted into the female connector of the pacemaker. One of the distal female lead connectors electrically connects the proximal end of a first unipolar lead to the cathode (−) terminal. The other distal female lead connector electrically connects the proximal end of a second unipolar lead to the anode (+) terminal. Hence, the lead adapter allows first and second unipolar implantable leads to function together as a bipolar lead. (In an alternate embodiment, two unipolar leads may be directly connected to a stimulation device having a bifurcated bipolar output connector (i.e., a connector having first and second receptacles for separately connecting the cathode (−) and the anode (+) terminal.)

In the alternative embodiment, the delivery means comprises a custom bifurcated lead adapter which is capable of delivering a stimulation pulse to two widely spaced sites simultaneously. Thus, the bifurcated lead adapter may be characterized as a Y-shaped insulated conductor having a single proximal bipolar male connector adapted to be inserted into the female connector of the pacemaker with a distal unipolar female connector and, preferably, a distal bipolar connector. The unipolar female lead connector electrically connects the proximal end of a unipolar lead to the cathode (−) terminal. The tip of the unipolar lead is in electrical contact with the translocated muscle tissue. The bipolar female lead connector electrically connects the proximal end of a bipolar lead to the cathode (−) and the anode (+) terminals. The bipolar lead is in electrical contact with the right (or left) ventricle in a conventional fashion. Thus, the custom bifurcated lead adapter enables sensing in the right ventricle, delivers a stimulation pulse in the right ventricle, and simultaneously delivers a stimulation pulse at the neurovascular site of the translocated muscle tissue using only a single-chamber VVT pulse generator.

While the custom bifurcated lead adapter described above has the benefit of bipolar sensing and programmable polarity, it would be apparent to one skilled in the art that the above-described embodiment may be modified to utilize two unipolar leads for pacing and sensing.

In alternate embodiments, the delivery means comprises a custom bifurcated lead having its proximal end configured similar to (a) the proximal end of the standard bifurcated bipolar lead adapter of the preferred embodiment, or (b) the proximal end of the custom bifurcated adapter of the alternate embodiment. Such a lead may be characterized as comprising an insulated, flexible conductor having a male proximal connector and first and second branches forming a general "Y" shape, the branches of the flexible conductor being joined near the proximal end. At the distal end of a first branch of the flexible conductor is a tip electrode in electrical contact with the translocated muscle. At the distal end of the second branch is a tip electrode in electrical contact with the ventricular muscle. Thus, when the proximal male connector is detachably connected to the stimulation device, depolarization of the tissue at the ventricular site is sensed and a stimulation pulse is delivered to the translocated muscle.

A method of stimulating a heart that has undergone cardiac myopiasty in accordance with the present invention uses a cardiac pacemaker operating in a single-chamber mode. Such method includes the steps of: (a) implanting a first electrode so as to contact ventricular tissue; (b) implanting a second electrode so as to contact translocated muscle tissue placed around the heart by the cardiac myopiasty; (c) electrically connecting both the first and second electrodes to an output terminal of a single-chamber pacemaker; and (d) operating the pacemaker in a triggered single-chamber mode of operation, so that depolarization of the ventricular tissue is sensed by the pacemaker, and so that a stimulation pulse generated by the pacemaker is delivered to the translocated muscle tissue. The triggered singlechamber mode of operation advantageously generates a stimulation pulse upon sensing a cardiac depolarization. Hence, a stimulation pulse is delivered to the translocated muscle tissue in synchrony with the sensed depolarization of the ventricular tissue, i.e., in synchrony with the contraction of the ventricles of the heart.

Thus it can be seen that the present invention advantageously provides various techniques, components and/or aids that may be used with a patient having undergone cardiac myopiasty. Each of these techniques, components and/or aids may be considered as a different embodiment of the invention. Such embodiments include, but are not necessarily limited to: (1) a stimulation system, including a stimulation device and delivery means (such as a bifurcated lead adapter with leads, or a bifurcated lead) that delivers a stimulation pulse to transplanted muscle tissue in synchrony with the heart's natural rhythm; (2) a bifurcated lead adapter that allows two stimulation leads to be connected to the single output connector of a single-chamber pacemaker; (3) a bifurcated lead that allows two widely spaced tissue stimulation locations, one of which may be an endocardial or epicardial location and the other of which may be translocated muscle tissue, to be electrically coupled to the single output connector of a single-chamber pacemaker; or (4) a method of stimulating a heart having undergone cardiac myopiasty.

It is a feature of the present invention to provide a more viable therapy for "advanced" congestive heart failure.

It is another feature of the present invention to provide a stimulation system that stimulates translocated muscle tissue wrapped around the heart in synchrony with the natural cardiac rhythm.

It is an additional feature of the invention to provide a stimulation system using a single-chamber pacemaker capable of sensing a muscle tissue depolarization and generating a stimulating pulse in synchrony therewith.

It is a further feature of the invention to provide a lead adapter for use with a single-chamber pacemaker that allows two leads to be electrically connected to the single output amplifier of a single-chamber pacemaker.

It is yet another feature of the invention to provide a bifurcated lead for use with a single-chamber pacemaker that allows the single output amplifier of the pacemaker to provide electrical stimulus to two widely spaced tissue locations.

It is still an additional feature of the invention to provide a method of stimulating a patient's heart that has undergone cardiac myopiasty.

BRIEF DESCRIPTION OF THE DRAWINGS

The above and other aspects, features and advantages of the present invention will become more apparent from the following Detailed Description of the Invention in conjunction with the following drawings, wherein:

FIG. 3A illustrates a pulse generator coupled to a Latissimus dorsi muscle for training the muscle in anticipation of translocating the muscle in a cardiomyoplasty procedure;

FIG. 3B shows an enlarged view of the intramuscular lead placed near the nerve bundle branches of the translocated tissue, as shown in FIG. 3A.

FIG. 4 shows a pulse generator system embodying various features of the present invention used in conjunction with a cardiomyoplasty procedure;

FIG. 9 illustrates an enlarged side view, shown partially in section and partially in schematic, of a bipolar lead adapter made in accordance with an alternative embodiment of the invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figures 1, 2:
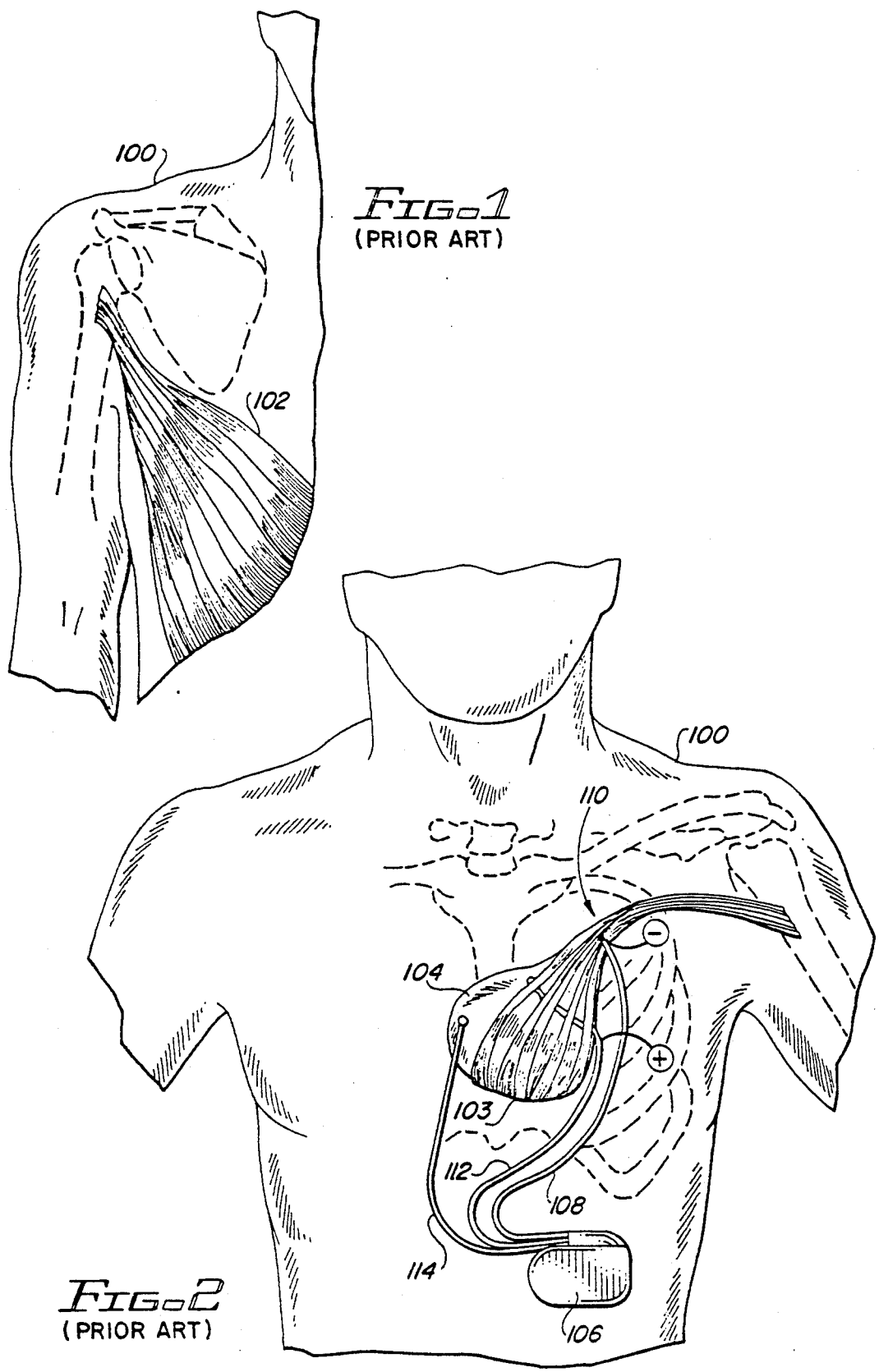
FIG. 1 shows the Latissimus dorsi muscle on the back of a human.
FIG. 2 is a view of a prior art pulse generator system used in conjunction with a cardiomyoplasty procedure.

As shown in FIG. 1, cardiac myoplasty comprises removing a section of skeletal muscle tissue, such as the Latissimus dorsi tissue 102, from the patient 100 and wrapping such tissue around the patient's heart. Advantageously, the Latissimus dorsi tissue 102 is a very strong muscle located in the patient's back, a section of which can be removed without seriously compromising the patient's ability to extend or move the arm at the level of the shoulder. The wrapped muscle tissue is then stimulated in synchrony with the heart's native contractions.

In FIG. 2, a dedicated myostimulator system is shown as is shown in the art. Such system includes a myostimulator device 106 in contact with the heart 104 of the patient 100, where the heart 104 has had translocated muscle tissue 103 wrapped therearound. A first intramuscular lead 108 is used cathodically (−) and placed near the nerve branches 110 of the translocated Latissimus dorsi tissue 103. A second intramuscular lead 112 is used anodically (+) and is placed distally in the muscle 103. A third lead 114 is used to sense native depolarization of the heart 104. Such placement of the leads 108, 112, and 114 is further illustrated in FIGS. 3A and 3B. Upon detection of a native depolarization through the sensing lead 114, the myostimulator device 106 initiates a synchronization delay, and then stimulates the translocated muscle 103 with a burst of stimulation pulses delivered through the leads 108 and 112.

As has been indicated, the present invention relates to a system and method of stimulating a heart that has undergone cardiac myopiasty. More specifically, the invention provides a system and method for stimulating translocated muscle tissue wrapped around the heart using a pacemaker that operates in a single-chamber triggered mode, e.g., the VVT mode.

A pacemaker is a medical device that is designed to supply stimulation pulses to a heart in order to cause the heart muscle tissue to contract. Most pacemakers include means for sensing when the muscle tissue is electrically activated (depolarized), which results in a contraction. The cardiac depolarization is manifested by an electrical signal or complex, as indicated, e.g., in an electrocardiogram (ECG), recorded at the skin of the patient, or an electrogram (EGM), recorded in or on the heart. The electrical complex in the ECG or EGM that indicates depolarization of the ventricle is generally referred to as an R-wave.

A typical pacemaker is capable of sensing ventricular depolarization (as recorded inside or on the heart), and is also capable of generating a stimulation pulse that causes the heart muscle tissue to contract. Typically, a pacemaker will be programmed to provide a stimulation pulse to the heart only if a natural contraction of the heart does not occur within a preset time period. In this way, stimulation pulses are provided only as needed, or "on demand", in order to maintain a prescribed rhythm (or rate) of the heart. Other operating modes of the pacemaker are also possible, such as the triggered mode described below.

The design, operation and use of implantable pacemakers is well known in the art, and will not be repeated herein. See, e.g., Furman et al., *A Practice of Cardiac Pacing*, Futura Publishing Co., Inc. Mt. Kisco, N.Y. (1986); U.S. Pat. No. 4,712,555, issued to Thornander et al. (relating to a physiologically responsive pacemaker); and/or U.S. Pat. No. 4,940,052, issued to Mann et al. (relating to a microprocessor-controlled pacemaker). The '555 and '052 patents are incorporated herein by reference.

One operating mode of a pacemaker particularly relevant to the present invention is the single-chamber triggered mode, such as the VVT mode. In the VVT mode, the pacemaker is configured to generate a ventricular stimulation pulse in response to sensing a ventricular depolarization. The sensing of the ventricular depolarization, as well as the delivery of a stimulation pulse to the ventricle, is accomplished by way of a pacemaker lead. Such pacemaker lead includes an elongate flexible conductor having a helically wound wire that electrically connects a distal electrode with a proximal lead connector. (Note, as used herein, the term "distal" refers to that end of the pacemaker lead that is farthest from the pacemaker; while the term "proximal" refers to that portion of the pacemaker lead closest to the pacemaker.) A suitable insulator surrounds and electrically insulates the flexible conductor, as well as isolates it from body fluids. The distal electrode is placed in contact with ventricular tissue. The proximal connector is detachably connected to the pacemaker.

In normal VVT operation, the depolarization of the ventricle is manifest by the generation of an R-wave, which R-wave is electrically coupled to the pacemaker through the distal electrode and pacemaker lead. The pacemaker responds by generating a ventricular stimulation pulse (sometimes referred to as a V-pulse) that is delivered to the ventricle through the pacemaker lead and distal electrode. This V-pulse finds the ventricle physiologically refractory (unable to contract because it has just contracted), which is normal for the triggered function. Traditionally, the triggered mode has been used primarily during follow-up and testing procedures, and has not usually been used for long-term pacing.

In accordance with the present invention, the triggered mode is advantageously used to assure that translocated muscle tissue (e.g., skeletal tissue, placed around the heart in accordance with cardiac myopiasty) is stimulated in synchrony with the natural contraction of the ventricle. To this end, there is shown in FIG. 4, a system 120 embodying various features of the present invention. Such system 120 includes a bifurcated bipolar lead adapter 122, such as is commercially available from Siemens Pacesetter, Inc., of Sylmar, Calif., as Model No. 501205. The adapter 122 has a male proximal connector 124 that is electrically connected to the bipolar output connector 126 of a single-chamber pacemaker 128. The adapter 122 further includes distal female connectors 130 and 132. The male proximal ends of standard unipolar pacing leads 134 and 136 are connected to the female connectors 130 and 132, respectively, of the adapter 122. A suitable unipolar pacing lead that may be used for the pacing leads 134 and 136 is the Model 1015M pacing lead (passive fixation) or the Model 1028 T pacing lead (active fixation), both of which are also commercially available from Siemens Pacesetter, Inc.

The distal electrode of the unipolar pacing lead 134 is electrically connected to ventricular tissue of the patient's heart 104 in a conventional manner. It is noted that such connection may be made either endocardially or epicardially. The distal electrode of pacing lead 136, on the other hand, is electrically connected to the translocated muscle tissue 103. Alternately, the distal electrode of pacing lead 136 may be placed in close proximity to the neurovascular bundle 138 leading to the translocated tissue. It is noted that, in some configurations, it may be desirable to connect the distal electrode of pacing lead 136 directly to an appropriate location on the translocated muscle tissue. Therefore, as used hereinafter, the term "translocated muscle" will refer to any part of the skeletal muscle which is wrapped around the heart, including the neurovascular bundle leading to the translocated muscle and the nerves which innervate the muscle.

As shown in FIG. 4, in the preferred embodiment, the lead 134 is connected through the adapter 122 to the ring terminal of the pacemaker's bipolar output connector 126. Similarly, the lead 136 is connected through the adapter 122 to the pin terminal of the pacemaker's bipolar output connector 126. If the pacemaker is programmed for bipolar stimulation, the distal electrode of the lead 134 (in contact with ventricular tissue) acts as the anode (+) and the distal electrode of the lead 136 (in contact with the translocated muscle tissue) acts as the cathode (−). If the pacemaker is programmed for unipolar stimulation, a reference electrode (such as the pacemaker case 129) acts as the anode (+) and the distal electrode of the lead 136 (in contact with the translocated muscle tissue) acts as the cathode (−). Sensing may be likewise programmed to unipolar mode (i.e., between the distal electrode of the lead 134 in contact with the ventricular tissue and the pacemaker case 129) or bipolar mode (i.e., between the distal electrode of lead 134 in contact with the right ventricle and the distal electrode of the lead 136 in contact with the translocated muscle tissue).

In operation, the pacemaker 128 operates in a single-chamber VVT mode. As such, the system 120 provides for both sensing of the R-wave within the ventricle, and delivery of the V-pulse to the translocated tissue, in synchrony with the sensing of the R-wave. As mentioned above, the pacemaker is capable of programmably generating either a single pulse or a pulse train, comprising a burst of closely-spaced pulses. Hereinafter, any reference to "a stimulus" implies either a single pulse or a pulse train. Hence, the bipolar bifurcated lead adapter 122, in conjunction with the unipolar leads 134 and 136 connected thereto, provides a means for electrically connecting both of the distal electrodes of the pacing leads (connected to widely-spaced tissue locations) to the bipolar in-line output connector 126 of the pacemaker 128.

Figure 5:
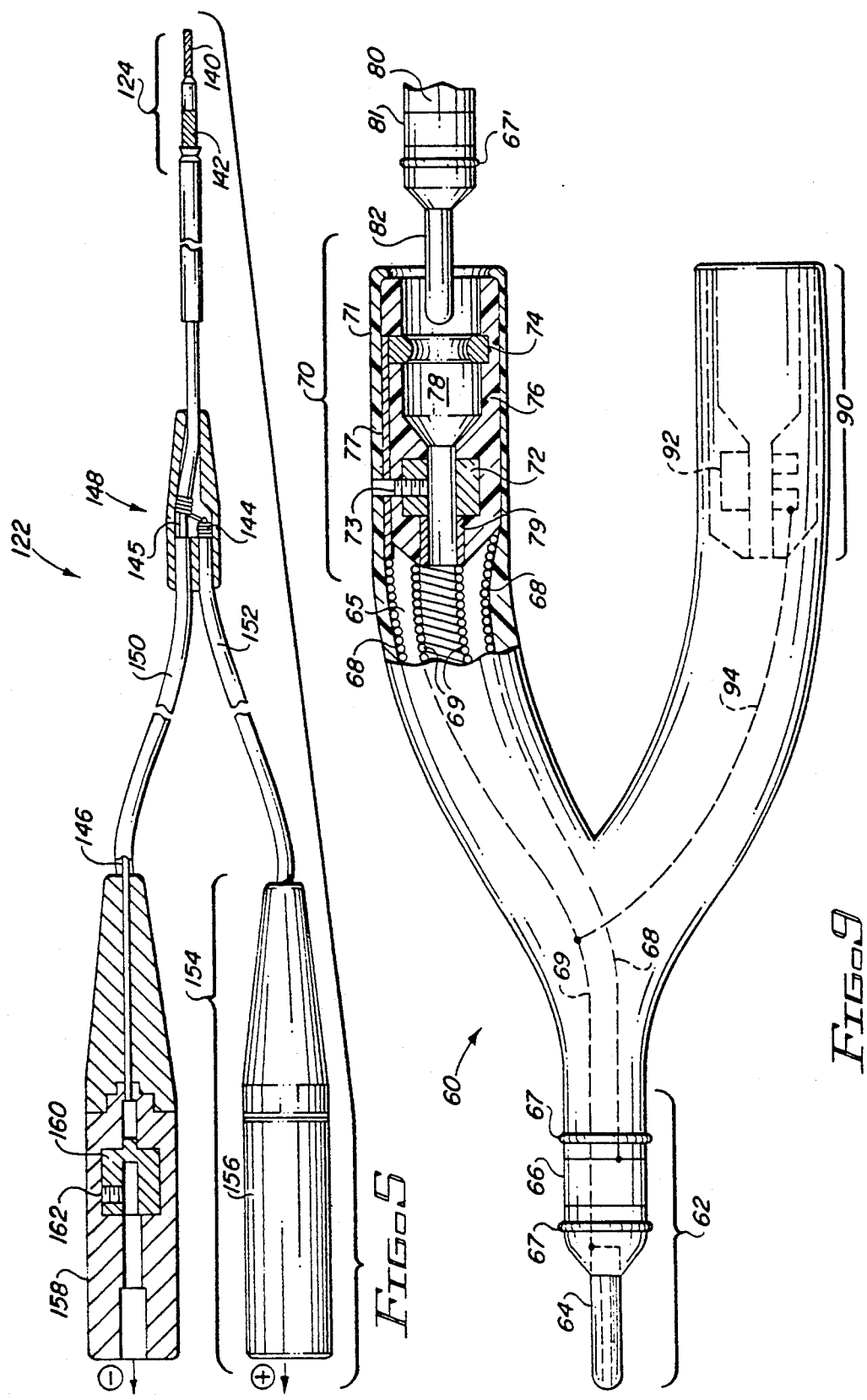
FIG. 5 shows bifurcated bipolar lead adapter that may be used with conventional unipolar leads in accordance with the teachings of the present invention.

In FIG. 5, a detailed view is shown of the bipolar bifurcated lead adapter 122 used in the preferred embodiment of the invention. The adapter 122 includes a proximal male connector 124 adapted to be inserted into the standard bipolar in-line output connector of the pacemaker. The male connector 124 includes a proximal pin terminal 140 and a proximal ring terminal 142. In general, the adapter has a "Y" shape. The proximal end of the adapter 122 includes two helically wound conductors 144 and 146. The conductor 146 is wound to have a smaller diameter than the wound conductor 144 so that the conductor 146 fits inside of the wound conductor 144, with a layer of insulation 145 therebetween. The conductor 146 is connected to the proximal pin terminal 140, and the conductor 144 is connected to the proximal ring terminal 142. About midway along the length of the adapter 122, at point 148, the outer conductor 144 breaks away from the inner conductor 146. The inner conductor 146 continues in a first branch 150 of the adapter 122, and the outer conductor 144 continues in a second branch 152 of the adapter 122. At a distal end 154 of the adapter 122, each conductor 144 and 146 is respectively connected to an appropriate female connector 156 and 158. Such female connectors may be of conventional design, each being adapted to receive the proximal male connector of a unipolar pacing lead. As seen in the cutaway portion of the connector 158, such female connectors 156 and 158 include a conductive block 160 to which the conductors 146 and 144, respectively, are electrically and physically connected (typically by crimping). A set screw 162 allows a firm physical and electrical connection to be made with the proximal pin terminal of the unipolar lead once such terminal is inserted therein.

Figure 6:
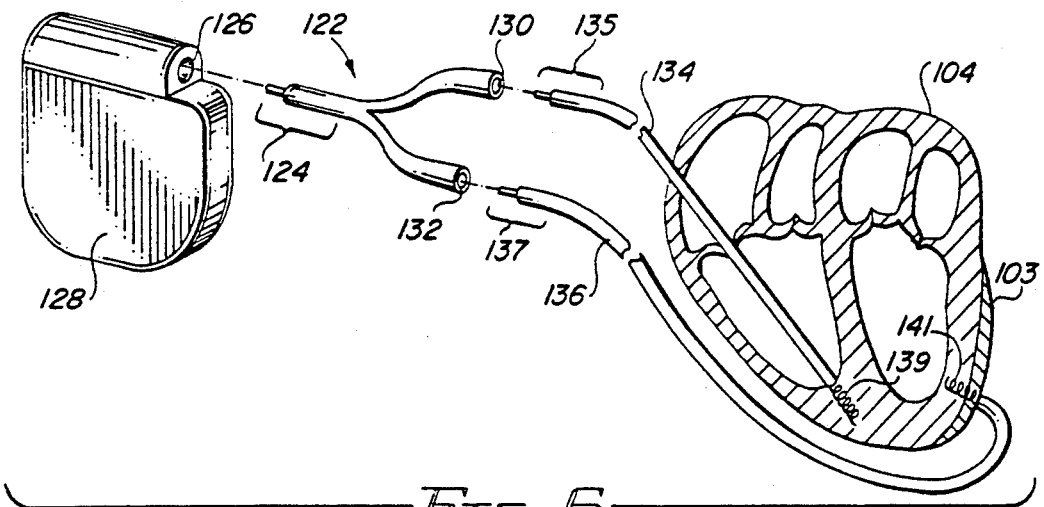
FIG. 6 illustrates a pacing system using a bifurcated lead adapter made in accordance with the present invention.

FIG. 6 shows one method in which the stimulating system of the present invention may be implemented using the bifurcated bipolar lead adapter 122. As seen in FIG. 6, the proximal male connector 124 of the adapter 122 is inserted into the bipolar output connector 126 of the single-chamber pacemaker 128. The adapter 122 has two female connectors 130 and 132, which are configured to receive proximal male connectors 135 and 137 of the leads 134 and 136, respectively. Thus, when the male connector 124 of the adapter 122 is inserted into the bipolar output connector 126 of the pacemaker 128, and when the proximal connector 135 of the lead 134 is inserted into the female connector 130, and the proximal connector 137 of the lead 136 is inserted into the female connector 132, lead 134 and 136 are electrically connected to the ring and pin terminals, respectively, of the bipolar output connector 126 of the pacemaker 128.

As shown in FIG. 6, a distal tip electrode 139 of the lead 134 is secured or positioned within the right ventricle of a patient's heart 104, in conventional manner. (Alternately, the distal tip electrode 139 could be secured or positioned on or to epicardial ventricular tissue.) In contrast, a distal tip electrode 141 of the lead 136 is secured to translocated skeletal muscle tissue 103 that has been wrapped around the left ventricle of the heart 104 using cardiac myopiasty techniques.

Thus, both the tissue location within the right ventricle and the tissue location in contact with the translocated tissue are simultaneously disposed to be in electrical contact with the pacemaker circuits through the pacemaker output connector 126. Hence, natural electrical cardiac activity occurring within the right ventricle is sensed across the tip electrodes 139 and 141 and is communicated to the pacemaker through the leads 134 and 16 and the adapter 122. The sensed ventricular activity triggers the pacemaker 128 to generate a stimulus. The pacemaker 128 may be programmed to deliver the stimulus in either a unipolar mode (wherein the case acts as the return electrode) or in a bipolar mode (wherein the tip electrode 139 acts as the return electrode). Thus, in this manner, the translocated skeletal tissue is stimulated to contract synchronously with the natural ventricular depolarization, thereby achieving the desired effect.

Figure 7:
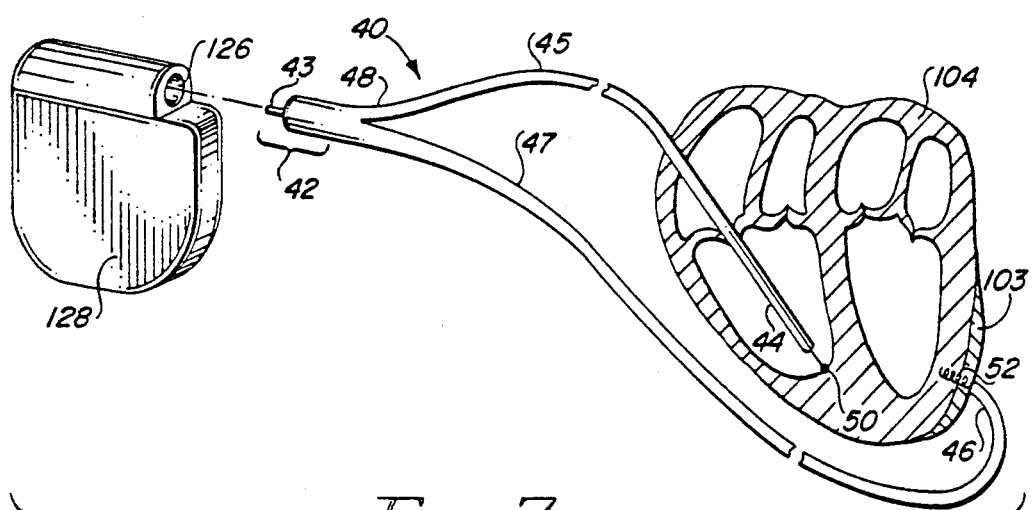
FIG. 7 is illustrates a pacing system using a bifurcated lead made in accordance with one embodiment of the present invention.

In an alternate embodiment, shown in FIG. 7, instead of employing the bifurcated bipolar lead adapter 122 and two standard unipolar pacing leads 134 and 136 (as shown in FIG. 6), the present invention may also use a bifurcated bipolar lead 40. As seen in FIG. 7, the bifurcated lead 40 includes an insulated flexible conductor 48 having a proximal end 42 and two distal ends 44 and 46. Electrodes 50 and 52 at the distal ends 44 and 46, respectively, are electrically connected to a bipolar output connector 126 by way of respective branches 45 and 47 of the flexible conductor 48. The flexible conductor 48 thus assumes a "Y" shape, with the branches 45 and 47 being joined near (e.g., within a few centimeters) the proximal end 42.

The proximal end 42 of the lead 40 is constructed identical to the proximal male connector 124 of the adapter 122. The distal electrode 50 is positioned within the ventricle of the heart 10 so as to make contact with ventricular tissue. Similarly, the distal electrode 52 is positioned so as to make electrical contact with the translocated muscle tissue 103. The lead 50 functions identical to the adapter 122 when connected to the two unipolar leads 134 and 136. That is, the distal electrode 50 acts as the anode (+) and the distal electrode 52 acts as the cathode (−). Either or both of these electrodes may utilize active fixation means (e.g., a screw-in helix tip) in order to hold the electrode to a desired tissue stimulation location. Such positive fixation means are commonly used with implantable pacemaker leads. Passive fixation means, such as tines or fins, may also be used, particularly in connection with the electrode 50 when such electrode is placed in contact with endocardial tissue.

Thus, in operation, natural ventricular depolarization (i.e., an R-wave) is sensed by the pacemaker across electrodes 50 and 52. When operating in a triggered mode, a stimulus is generated by the pacemaker 128 upon sensing such R-wave. The pacemaker 128 may be programmed to deliver the stimulus in either a unipolar mode (e.g., between tip electrode 52 and the case) or a bipolar mode (e.g., between the tip electrode 52 and the tip electrode 50). Such stimulus thus stimulates the translocated muscle tissue 30, causing it to contract simultaneously with the sensed depolarization of the ventricle.

In the prior art, bifurcated bipolar leads have a single cable for the major portion of the lead and two male terminal pins with the bifurcation occurring only a few centimeters from the terminal pins so that separate conductors are used in each branch of the bifurcation. Unlike bifurcated bipolar leads of the prior art, the bifurcated lead 40 of the present invention has its bifurcation point 48 within a short segment of the common terminal pin 43 so that the branches 45 and 47 continue for a substantial length, e.g., 40 to 60 cm.

Different versions of bifurcated leads may be manufactured, as required, in order to provide different types of branch lengths, electrodes and fixation means at the tips of each branch. For example, one branch intended for use on the ventricle may have either an epicardial screw or passive fixation elements with a multiplicity of different electrode materials (platinum iridium, activated carbon, titanium nitride, etc.). The other branch intended for use with the translocated skeletal muscle tissue may also have an appropriate fixation element (epicardial screw, suture loops, etc.) and an appropriate electrode material (titanium nitride, activated carbon, stainless steel, etc.), and various lengths. The bifurcated lead 40 and the Y-shaped lead adapter 122 are constructed using the same techniques and methods used to construct implantable pacemaker leads. Such construction techniques are known in the art.

Figure 8:
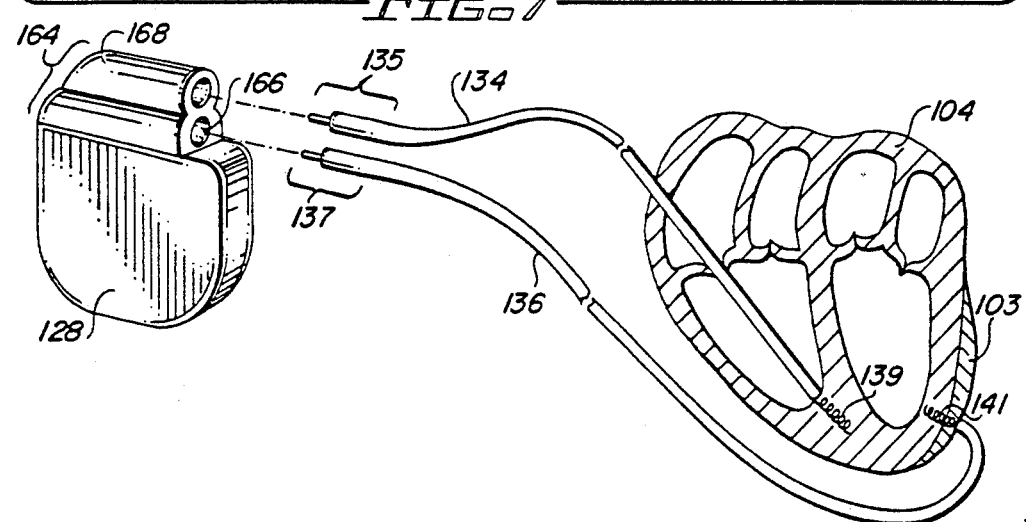
FIG. 8 is illustrates a pacing system using a pacemaker having a bifurcated output connector made in accordance with another embodiment of the present invention.

In FIG. 8 is another embodiment for the delivery system. As shown in FIG. 8, the pacemaker 128 has a bifurcated bipolar connector 164 which includes a first and a second receptacle 166 and 168 corresponding to the cathode (+) and anode (−) terminals. The proximal male connector 137 of lead 136 is slidably inserted into the first receptacle 166. The proximal male connector 134 of lead 135 is slidably inserted into the second receptacle 168. The system shown in FIG. 8 functions identically to that system shown in FIG. 6. While the pacemaker shown in FIG. 8 may be slightly larger in size, it eliminates the need for the adapter 122 (FIG. 6) and achieves the same result.

The basic features of an alternate stimulation system are illustrated in FIG. 9. FIG. 9 shows an enlarged side view, shown partially in section and partially in schematic, of an alternate bipolar lead adapter 60 made in accordance with the present invention. A proximal end 62 of the adapter 60 includes all of the elements of the proximal end of a conventional bipolar lead. These elements include a connector pin 64 and a ring electrode 66. Sealing ridges 67 may also be used to help seal the proximal end 62 into an output connector of a pacemaker. All of these elements may be sized and spaced in accordance with accepted industry standards for pacemaker leads and connectors, such as the VS-1 standard, described, e.g., in Calfee et al., supra, or other defined standards.

A first and a second distal female connector 70 and 90 may be provided at the distal ends of the adapter 60. The first distal female connector 70 is constructed using the same techniques and standards as are used in constructing the output connector of a pacemaker. See, e.g., U.S. Pat. Nos. 4,764,132 and 4,848,346, incorporated herein by reference. Essentially, this construction includes a first conductive block 72 and a second conductive ring terminal 74. The conductive block 72 has a hole through its center adapted to receive a proximal connector pin 82 of a conventional bipolar or unipolar lead 80. The conductive block 72 and ring terminal 74 are spaced apart a prescribed distance by means of a nonconductive substrate 76. The nonconductive substrate 76 is shaped and formed so as to be compatible with the applicable standard of the pacemaker lead. Thus, the substrate is formed and/or machined so as to have a cavity 78 therein into which the proximal end of a pacemaker lead may be inserted.

Typically, the conductive block 72 has a set screw 73 therein, or equivalent. This set screw provides a means for detachably securing the connector pin 82 of the lead 80 within the connector 70. A set screw may also be used to make secure electrical connection with the ring electrode 81; however, in the preferred embodiment, a canted coil garter spring is used. For a more complete description of canted coil garter springs, see U.S. Pat. No. 5,012,807, issued May 7, 1991, which patent is assigned to the same assignee as is the present application and is hereby incorporated herein by reference.

A conductor 77 electrically connects the ring terminal 74 to a flexible conductor 68. The flexible conductor 68 passes through the length of the adapter 60 and is electrically and mechanically secured to the proximal ring electrode 66. The conductor 68 is realized using a helically wound conductive wire, as is commonly used within pacemaker leads. Another conductor 79 electrically connects the block 72 to a second flexible conductor 69. This second flexible conductor 69 is also realized using a helically wound conductive wire, and is typically wound so as to have a smaller diameter than the wound conductor 68. Thus, the conductor 69 resides inside of the lumen created by the conductor 68. An inner insulating sheath 65 is positioned between and separates the conductors 68 and 69 so that they are electrically isolated from each other. An outer insulating sheath 71 surrounds the conductor 68. This type of coaxial construction is commonly used in bipolar pacemaker leads. It should be understood, however, that the present invention is not limited to coaxial lead construction. For example, the bifurcated lead 40 or the adapter 122 or 60 could consist of a multilumen construction in which the flexible conductors 68 and 69 are inserted into separate lumens, or holes, within an insulating tube of biocompatible polymer material, as is well known in the art.

The second distal connector 90, is preferably, a unipolar connector and is constructed using the same techniques and standards as are used in constructing a unipolar output connector of a pacemaker. This construction is substantially identical to the bipolar construction described above, with the omission of the ring terminal 74. Thus, the ring terminal 90 includes a conductive block 92 which is electrically connected to a flexible conductor 94. The flexible conductor 94 passes through the length of the adapter 60 and is electrically and mechanically secured to the second flexible conductor 69. Thus, the second distal connector 90 is adapted to receive a unipolar lead.

Thus, in the alternate embodiment, the adapter 60 may be used to replace the adapter 122 shown in FIG. 6. The pacemaker 128 still operates in a single-chamber triggered mode, however, the lead adapter 60 is used to couple the output channel 126 of the single-chamber pacemaker 128 to stimulate two widely spaced sites simultaneously. The proximal end 137 of the first unipolar lead 136 is received into the second distal connector 90 and the distal tip 141 is placed at the translocated muscle tissue 103 and is configured to function as a first cathode (−). The distal tip 139 of the second lead 134 (either unipolar or bipolar) is placed in contact with the right ventricle of the heart and is configured to function as either a conventional unipolar or bipolar lead, as desired. Thus, the single-chamber pacemaker is configured to sense in the right ventricle like a conventional pacemaker, trigger a stimulus in the right ventricle, and simultaneously trigger a stimulus at the translocated muscle tissue. Since the ventricular tissue is refractory at this time, the triggered stimulus in the ventricle has no effect thereon.

Alternately, the lead 40, or the adapter 122 or 60, could be made using a "thin bipolar" configuration as described in U.S. Pat. application No. 07/716,032, filed Jun. 14, 1991, assigned to the same assignee as is the present application and incorporated herein by reference. "Thin bipolar," as used in the above-identified patent application, refers to a coaxial bipolar lead wherein individual filars are electrically insulated from each other by a thin polymer insulative coating and then coaxially wound together. The insulative coating may be the polymer materials sold under the trademarks TEFLON and TEFZEL, manufactured by DuPont, which materials have good electrical insulating properties without adding significant bulk. Typically, each conductor is comprised of two filars for redundancy.

It is noted that the lead adapter 60 (as described above with reference to FIG. 7) is designed for use with one unipolar and one bipolar lead. In fact, a similar (yet simpler) construction may be used to make two unipolar connectors in such an adapter. Other embodiments may employ a bipolar output connector in both arms of the adapter. (It is noted that a unipolar lead can normally be inserted into a bipolar connector, in which case the ring electrode is not used.)

One advantage of using either the adapter 122 (FIG. 5) or the adapter 60 (FIG. 9) is that standard commercially available pacing leads may be used therewith. These leads may be active fixation leads or passive fixation leads; and they may have electrodes made from platinum-iridium, activated carbon, titanium nitride, or other commonly used materials. As indicated above in connection with FIG. 4, the anodic lead is placed endocardially in or epicardially on the ventricle, and the other, cathodic lead is placed on the translocated tissue. Both leads are surgically tunneled in conventional manner to the pacemaker pocket where they are connected to the adapter 122 or 60, and where the bifurcated adapter is connected to the pacemaker.

As a method of stimulating a patient's heart that has undergone cardiac myoplasty, a first step requires placing the distal electrodes of the leads (or bifurcated) lead in contact with the desired tissue. Next, the leads or lead are connected to the output connector of the pacemaker, giving special attention to the fact that each electrode is to have an appropriate polarity, as described above. If separate leads are used, the bifurcated adapter of the present invention makes this connection possible. If the bifurcated lead is used, its single proximal connector is connected directly to the pacemaker.

The treatment method next involves operating the pacemaker in a VVT mode. This mode causes a stimulus to be released in response to a sensed R-wave. Thus, a native R-wave is detected across the ventricular electrode and the other electrode. In response to sensing the R-wave, the pacemaker releases an output stimulus consistent with the VVT triggered mode of operation, which pulse is applied across the electrodes to stimulate the translocated muscle tissue. Stimulation of the translocated muscle tissue causes it to contract, thereby assisting the overall heart contraction by squeezing the ventricle.

Advantageously, use of a single-chamber pacemaker operating in the VVT mode for both sensing the natural ventricular contraction and stimulating the translocated tissue in synchrony therewith reduces the cost associated with this type of treatment. While a dual chamber pacemaker could be used for this same purpose, as described above, a dual chamber pacemaker is significantly more expensive, larger and heavier than a single-chamber pacemaker.

Thus, from the above, it is seen that the present invention provides a viable therapy for advanced congestive heart failure. Such therapy advantageously stimulates muscle tissue translocated around the heart in synchrony with a natural cardiac rhythm.

It is also seen from the above description that the invention provides a stimulation system that stimulates translocated muscle tissue in a coordinated manner in synchrony with the heart's natural rhythm.

It is further seen that the present invention provides, in one embodiment, a lead adapter for use with a single-chamber pacemaker that allows two otherwise conventional pacing leads to be electrically connected to the single output connector, and hence the single output amplifier of the singlechamber pacemaker. In another embodiment, the invention provides a lead for use with a singlechamber pacemaker that allows the single output amplifier of the pacemaker to be in simultaneous electrical contact with two widely spaced tissue locations.

Moreover, as additionally seen from the above, the present invention provides a method of stimulating a patient's heart that has undergone cardiac myoplasty using a single-chamber pacemaker operating in a triggered mode.

While the invention herein disclosed has been described by means of specific embodiments and applications thereof, numerous modifications and variations could be made thereto by those skilled in the art without departing from the scope of the invention set forth in the claims.

What is claimed is:

1. A stimulation system for stimulating translocated muscle tissue in a patient having cardiac myoplasty, comprising:
   an implantable pulse generator having means for sensing cardiac signals and pulse generating means for synchronously triggering a stimulus in response thereto, the implantable pulse generator having a bipolar output channel with first and second output terminals, the sensing means being coupled to the first and second output terminals so that cardiac signals are sensed therebetween, the pulse generating means being coupled to the first and second output terminals so that the first and second output terminals act as a cathode and an anode, respectively; and
   delivery means having a first distal electrode for contact with a first tissue location and a second distal electrode for contact with a second, widely-spaced, tissue location, the first and second distal electrode in electrical contact with the first and second output terminals, respectively, for sensing cardiac signals at the first tissue location and delivering the stimulus generated by the pulse generator to the second, widely-spaced, tissue location, the first tissue location including translocated muscle tissue, the second, widely-spaced, tissue location including ventricular tissue;
   whereby the delivery means enables the implantable pulse generator to sense cardiac signals originating in the ventricles and to synchronously trigger the translocated muscle tissue, at the widely-spaced tissue location, to contract.

2. The stimulation system as set forth in claim 1, wherein the bipolar output channel comprises:
   a connector top having a receptacle for receiving the delivery mean, the receptacle having the first and second output terminals axially disposed therein and electrically isolated therebetween, so that the first and second output terminals are in-line.

3. The stimulation system as set forth in claim 2, wherein the delivery means comprises:
   a first stimulation lead having a first proximal male connector electrically connected to the first distal electrode;
   a second stimulation lead having a second proximal male connector electrically connected to the second distal electrode; and
   a Y-shaped lead adapter having a third proximal male connector dimensioned to fit within the receptacle in the connector top, the adapter further having first and second distal female connectors dimensioned to receive the first and second proximal male connectors of the first and second stimulation leads, respectively, the third male connector includes a pin terminal and a ring terminal, the pin and ring terminal being electrically connected to the first and second distal female connectors, respectively, so that when the third proximal male connector is inserted into the bipolar output channel of the implantable pulse generator, and when the first and second leads are inserted into the first and second distal female connectors, respectively, the first and second distal electrodes are electrically connected to the first and second output terminals.

4. The stimulation system, as set froth in claim 3, wherein the first and second stimulation leads comprise first and second unipolar leads, respectively.

5. The stimulation system as set forth in claim 2, wherein the delivery means comprises:
a Y-shaped lead having a proximal male connector dimensioned to fit within the receptacle in the connector top, the proximal male connector having a first and a second branch at a distal end thereof, the first and second branches having the first and second distal tip electrodes attached thereto, the proximal male connector includes a pin terminal and a ring terminal, the pin and ring terminal being electrically connected to the first and second distal tip electrodes, respectively, so that when the proximal male connector is inserted into the bipolar output channel of the implantable pulse generator, the first and second distal tip electrodes are electrically connected to the first and second output terminals, respectively.

6. The stimulation system as set froth in claim 1 further comprising:
a case electrode; and
switching means for programmably selecting one of the case electrode or the first distal electrode of the first stimulation lead to act as a reference electrode for the sensing means;
whereby the sensing means senses cardiac signals between the selected reference electrode and the second distal electrode of the second stimulation lead.

7. The stimulation system as set forth in claim 1, further comprising:
a case electrode;
switching means for programmably selecting as the anode one of the case electrode or the second distal electrode of the second stimulation lead; and
whereby the pulse generating means generates a stimulus between the selected anode and the first distal electrode of the first stimulation lead.

8. The stimulation system as set forth in claim 1, wherein:
the bipolar output channel comprises a connector top having a first and a second female receptacle, the first female receptacle having the first output terminal therein, the second female receptacle having the second output terminal therein; and
the delivery means comprises a first and a second stimulation lead, each lead having a proximal male connector electrically connected to a distal tip electrode, the tip electrode of the first lead for contact with translocated tissue, the tip electrode of the second lead for contact with the ventricular tissue, so that when the proximal male connectors of the first and second leads are inserted into the first and second female receptacles of the implantable pulse generator, respectively, the distal tip electrodes of the first and second leads are electrically connected to the first and second output terminals, respectively.

9. The stimulation system as set forth in claim 1, wherein the stimulus generated by the pulse generating means comprises one of a single pulse or a burst of closely-spaced pulses.

10. A stimulation system for controlling a patient's heart having translocated muscle tissue wrapped therearound by cardiac myoplasty, comprising:
stimulation/sensing means, having an input/output connector having a cathodic and an anodic terminal, for sensing the depolarization of the ventricle and for generating a stimulus in response thereto;
first conducting means having a distal end for contact with the ventricle of a heart and a proximal end electrically connected to the anodic terminal; and
second conducting means having a distal end for contact with the translocated muscle tissue and a proximal end electrically connected to the cathodic terminal, the translocated tissue being widely-spaced from the ventricular tissue;
whereby cardiac signals are sensed and a stimulus is delivered between two widely-spaced tissue sites.

11. The stimulation system as set forth in claim 10, wherein the first and second conducting means comprise:
a first and second pacing lead; and
an adapter configured to connect the first and second pacing leads to the anodic and the cathodic terminals, respectively, of the input/output connector of the stimulation/sensing means.

12. The stimulation system, as set forth in claim 11, wherein the first and second pacing leads comprise unipolar pacing leads.

13. A stimulation system for controlling a patient's heart having translocated muscle tissue wrapped therearound by cardiac myoplasty, comprising:
stimulation/sensing means, having an input/output connector having a cathodic and an anodic terminal, for sensing the depolarization of the ventricle and for generating a stimulus in response thereto; and
a delivery means having a first tip electrode for contact with translocated muscle tissue and a second tip electrode for contact with ventricular tissue, the first and second tip electrode being electrically connected to the cathode, the delivery means further having a distal ring electrode for contact with the ventricular tissue and electrically connected to the anode;
whereby the delivery means enables the implantable pulse generator to generate a stimulus simultaneously to the translocated muscle tissue and to the ventricular tissue in response to a sensed cardiac signal.

14. A method of stimulating a heart having undergone cardiac myoplasty using a pacemaker, the pacemaker having an output connector with a first and a second terminal, the cardiac myoplasty including translating muscle tissue from one body location and wrapping it around the outside of the ventricle of the heart, the method comprising the steps of:
(a) implanting a first electrode so as to contact ventricular tissue;

(b) implanting a second electrode so as to be coupled to the translocated muscle tissue;

(c) electrically connecting the first electrode to the first terminal of the output connector of the pacemaker;

(d) electrically connecting the second electrode to the second terminal of the output connector of the pacemaker;

(e) programming the pacemaker to sense cardiac signals and to provide a stimulus across the first and second electrode in response thereto so that the translocated muscle contracts in synchrony with sensing the ventricular depolarization.

15. The method as set forth in claim 14, wherein the translocated muscle tissue includes a neurovascular bundle, wherein:

step (a) comprises implanting the first electrode endocardically to contact the ventricular tissue; and step (b) comprises implanting the second electrode so as to contact the neurovascular bundle.

16. A stimulation system for stimulating translocated muscle tissue in a patient having cardiac myoplasty, comprising:

an implantable pulse generator having means for sensing cardiac signals and pulse generating means for synchronously triggering a stimulus in response thereto, the implantable pulse generator having a bipolar output channel, the bipolar output channel having first and second output terminals, the sensing means being coupled to eh first and second output terminals so that cardiac signals are sensed therebetween, the pulse generating means being coupled to the first and second output terminals so that the first and second output terminals act as a cathode and an anode terminal, respectively; and delivery means having a ring and a first tip electrode for contact with ventricular tissue and a second tip electrode for contact with the translocated muscle tissue, the first and second tip electrode in electrical contact with the first output terminal, the ring electrode in electrical contact with the second output terminal;

whereby the delivery means enables the implantable pulse generator to sense cardiac signals and to trigger an electrical stimulus simultaneously to the translocated muscle tissue and to the ventricular tissue.

17. The stimulation system as set forth in claim 16, wherein the delivery means comprises:

a first stimulation lead having a proximal pin and a proximal ring terminal electrically connected to the first tip and the ring electrode;

a second stimulation lead having a proximal pin terminal electrically connected to the second tip electrode; and a Y-shaped lead adapter having a proximal male connector and first and second distal female connectors, the proximal male connector including a pin and a ring terminal, the first and second female connectors dimensioned to receive the first and second stimulation leads, respectively, the first female connector having means for electrically connecting the proximal pin and the proximal ring terminals of the first stimulation lead to the pin and ring terminals of the adapter, the second female connector having means for electrically connecting the proximal pin terminal of the second stimulation lead to the pin terminal of the adapter, so that when the proximal male connector is inserted into the bipolar output channel of the implantable pulse generator, and when the first and second leads are inserted into the first and second female connectors, respectively, the tip electrodes of the first and second leads are electrically connected to the cathode terminal and the ring electrode is connected to the anode terminal.

18. The stimulation system as set forth in claim 17, wherein the implantable pulse generator further comprises:

a case electrode; and switching means for programmably selecting one of the case electrode or the ring electrode of the first stimulation lead to act as a reference electrode for the sensing means;

whereby the sensing means selectively senses cardiac signals in one of a unipolar fashion between the first tip electrode and the case electrode or in a bipolar fashion between the first tip and ring electrodes.

19. The stimulation system as set forth in claim 16, wherein the delivery means comprises:

a Y-shaped lead having a male connector at a proximal end dimensioned to fit within the bipolar output channel of the implantable pulse generator, the male connector including a pin terminal and a ring terminal, the lead further having first and second branches, the first branch having a distal tip electrode and a ring electrode electrically connected to the pin and ring terminals, the second branch having a distal tip electrode electrically connected to the pin terminal, the tip electrodes of the first and second branches for contacting the ventricular tissue and the translocated muscle tissue, respectively, so that when the male connector is inserted into the bipolar output channel connector of the implantable pulse generator, the tip electrodes of the first and second branches are electrically connected to the cathode terminal, and the ring electrode is connected to the anode terminal.

20. The stimulation system as set forth in claim 16, wherein the stimulus generated by the pulse generating means comprises one of a single pulse or a burst of closely-spaced pulses.

21. A stimulation system for stimulating translocated muscle tissue in a patient having cardiac myoplasty, comprising:

an implantable pulse generator having means for sensing cardiac signals and pulse generating means for synchronously triggering a stimulus in response thereto, the implantable pulse generator having a bipolar output channel with first and second output terminals, the implantable pulse generator further having a case electrode, the pulse generating means being coupled to the first output terminal and one of the case electrode or the second output terminal so that the first output terminal acts as a cathode, the sensing means being coupled to the second output terminal and one of the case electrode or the fist output terminal; and delivery means having a first distal electrode for contact with the a first tissue location and a second distal electrode for contract with a second, widely-spaced, tissue location, the first tissue location including translocated muscle tissue, the second, widely-spaced, tissue location including ventricular tissue, the first and second distal electrode in electrical contact with the first and second output terminals, respectively;

whereby the delivery means enables the implantable pulse generator to sense cardiac signals at a first tissue location and provide electrical stimulus to a second, widely-spaced, tissue location.

* * * * *